United States Patent [19]

Nozulak et al.

[11] Patent Number: 4,656,167
[45] Date of Patent: Apr. 7, 1987

[54] NAPHTHOXAZINES AND THEIR USE AS PSYCHOSTIMULATING AND ANTIDEPRESSANT AGENTS

[75] Inventors: Joachim Nozulak, Hartheim, Fed. Rep. of Germany; Rudolf K. A. Giger, Riehen, Switzerland

[73] Assignee: Sandoz Ltd., Basle, Switzerland

[21] Appl. No.: 850,999

[22] Filed: Apr. 11, 1986

Related U.S. Application Data

[63] Continuation of Ser. No. 743,511, Jun. 11, 1985, abandoned.

[30] Foreign Application Priority Data

Jun. 12, 1984 [DE] Fed. Rep. of Germany ....... 3421729
Mar. 8, 1985 [DE] Fed. Rep. of Germany ....... 3508263

[51] Int. Cl.$^4$ .................. A61K 31/535; C07D 265/34
[52] U.S. Cl. ................................... 514/227; 514/228; 514/232; 514/239; 544/101
[58] Field of Search ................ 544/101; 514/227, 228, 514/232, 239

[56] References Cited

U.S. PATENT DOCUMENTS 4,420,480  12/1983  Jones ................................ 544/101 X

OTHER PUBLICATIONS

Drandarov et al, Chemical Abstracts, vol. 100 (1984) 197839t.
Drandarov et al, Journal of Chromatography, 285 (1984), pp. 373–379.
Dantchev et al, Chemical Abstracts, vol. 77 (1972) 101,491f.
Stoichev et al, Chemical Abstracts, vol. 83 (1975) 71757b.
Dalev et al, Chemical Abstracts, vol. 85 (1977) 177339y.
Ivanov et al, Chemical Abstracts, vol. 89 (1978) 43,275y.

Primary Examiner—Richard L. Raymond
Attorney, Agent, or Firm—Gerald D. Sharkin; Robert S. Honor; Thomas O. McGovern

[57] ABSTRACT 3,4,4a,5,10,10a-hexahydro-2H-naphth[2,3-b]-1,4-oxazines are useful as psychostimulating and antidepressant agents.

17 Claims, No Drawings

NAPHTHOXAZINES AND THEIR USE AS PSYCHOSTIMULATING AND ANTIDEPRESSANT AGENTS

This is a continuation of application Ser. No. 743,511, filed June 11, 1985, now abandoned.

The invention relates to naphthoxazines.

The invention provides psychostimulating and/or antidepressant 3,4,4a,5,10,10a-hexahydro-2H-naphth[2,3-b]-1,4-oxazines in free base or acid addition salt form.

The basic compound 3,4,4a,5,10,10a-hexahydro-2H-naphth[2,3-b]-1,4-oxazine (also known in the literature as 2,4,4a,5,10,10a-hexahydro-4H-naphth[2,3-b]-1,4-oxazine or "naphthalane morpholine") and some N-substituted derivatives of this compound have been disclosed for the first time by L. Knorr in Liebigs Ann. Chem. 307, 171 (1899). Further N-substituted derivatives with analgesic and CNS depressant activity have been reported in the meantime. However, no 3,4,4a,5,10,10a-hexahydronaphth[2,3-b]-1,4-oxazine substituted in the aromatic ring and having pharmaceutical activity has been disclosed so far. Although some 6,9-disubstituted naphthoxazine-2-ones are known from K. Drandarov et al., Journal of Chromatography, 285 (1984), p. 374, only procedures resulting in reactions selective for some of the functional groups of these and related compounds are reported there.

According to the present invention it has now surprisingly been found that these 3,4,4a,5,10,10a-hexahydro-naphth[2,3-b]-1,4-oxazines substituted in the aromatic ring, hereinafter referred to as new compounds, exhibit a totally unexpected profile of activity, i.e. psychostimulating and antidepressive activity.

The new compounds have the following structure:

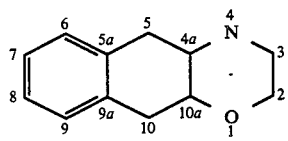
A

This basic structure may be substituted by pharmacologically acceptable groups. Examples of such groups are well known to the skilled man. In particular the 2, 4, 6, 7, 8 and 9 positions may be substituted. The compounds bearing on the aromatic ring of structure A (positions 6 to 9) at least one substituant chosen from the group alkoxy, alkylthio, alkylsulfoxide, alkylsulfone, alkyl, hydroxy, halogen and trifluoromethyl are preferred.

The new compounds possess at least two asymmetrical carbon atoms in positions 4a and 10a. They may therefore appear in racemic or optically active forms. The invention relates to both the racemates and the optically active forms.

In positions 4a and 10a the new compounds may have the cis configuration or the trans configuration. The compounds with the trans configuration are preferred.

The new compounds may be present in free base form or as acid addition salts. The invention relates to both the free bases and the addition salt forms. Examples of suitable pharmaceutically acceptable acid addition salt forms are the hydrochlorides, hydrobromides, hydrogen maleates and hydrogen fumarates.

The invention relates in particular to compounds of formula I

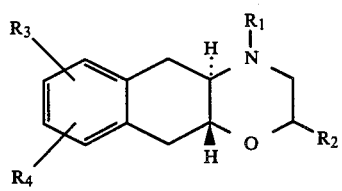

wherein
R$_1$ and R$_2$ independently are hydrogen or (C$_{1-4}$)alkyl,
R$_3$ is hydroxy or (C$_{1-4}$)alkoxy and
R$_4$ is (C$_{1-4}$)alkylthio, (C$_{1-4}$)alkylsulfoxide, (C$_{1-4}$)alkylsulfone, chlorine, bromine, iodine or trifluoromethyl, in free base or acid addition salt form.

The compounds of formula I have the trans configuration in positions 4a and 10a. Following accepted nomenclature conventions, the above representation of formula I embraces the trans isomers with the configuration IA as well as those with the configuration IB.

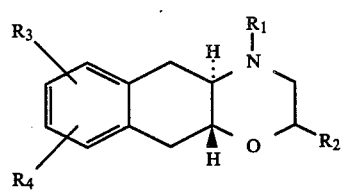

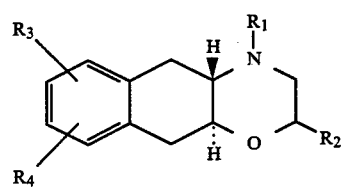

As indicated above, the formula I also covers to the corresponding racemates.

In the case where R$_2$ is not hydrogen, again both possible isomers as well as the corresponding racemates are covered by the invention.

Any alkyl, alkoxy, alkylthio, alkyl—SO— or alkyl—SO$_2$— preferably has one or two carbon atoms and especially one carbon atom.

R$_3$ and R$_4$ preferably are in para position for each other, i.e. in positions 6 and 9.

In a group of compounds of formula I,
R$_1$ and R$_2$ independently are hydrogen or (C$_{1-4}$)alkyl,
R$_3$ and R$_4$ are in para position,
R$_3$ is (C$_{1-4}$)alkoxy and
R$_4$ is chlorine, bromine, iodine or (C$_{1-4}$)alkylthio.

The following significances are preferred:
R$_1$ is (C$_{1-4}$)alkyl, particularly methyl;
R$_2$ is hydrogen;
R$_3$ is (C$_{1-4}$)alkoxy, particularly methoxy;
R$_4$ is chlorine, bromine, iodine or (C$_{1-4}$)alkylthio, particularly iodine or methylthio.

The present invention also provides a process for the production of the new compounds in free base or acid addition salt form, which includes the step of (a) introducing in 2,3 position of a correspondingly substituted 1,4-dihydro-naphthaline an optionally substituted aminoethyleneoxy bridge, or (b) reducing in 3 position a correspondingly substituted 2,4,4a,5,10,10a-hexahydro-3H-naphth[2,3-b]-1,4-oxazin-3-one, or
(c) substituting in 4 position a correspondingly substituted 4-unsubstituted 3,4,4a,5,10,10a-hexahydro-2H-naphth[2,3-b]-1,4-oxazine, or
(d) converting a thus obtained naphthoxazine into a further 3,4,4a,5,10,10a-hexahydro-2H-naphth[2,3-b]-1,4-oxazine substituted in the aromatic ring and recovering the resultant naphthoxazine in free base or acid addition salt form.

The invention provides in particular a process for the production of a compound of formula I or an acid addition salt thereof, which includes the step of
(a) introducing in 2,3 position of a 1,4-dihydro-naphthaline of formula IX

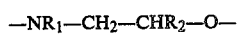

IX wherein $R_3$ is hydroxy or $(C_{1-4})$alkoxy, an aminoethyleneoxy bridge of formula $$-NR_1-CH_2-CHR_2-O-$$

wherein $R_1$ and $R_2$ are as defined above, or
(b) reducing in 3 position a 2,4,4a,5,10,10a-hexahydro-3H-naphth[2,3-b]-1,4-oxazine-3-one of formula IV

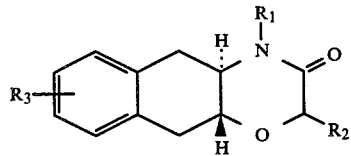

IV wherein $R_1$, $R_2$ and $R_3$ are as defined above, or
(c) alkylating in 4 position a 3,4,4a,5,10,10a-hexahydro-2H-naphth[2,3-b]-1,4-oxazine of formula III

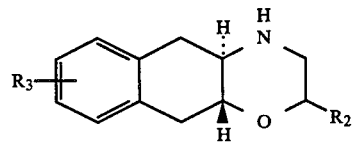

III wherein $R_2$ and $R_3$ are as defined above, or
(d) converting a 3,4,4a,5,10,10a-hexahydro-2H-naphth[2,3-b]-1,4-oxazine into a compound of formula I, and recovering the resultant compound of formula I in free base or acid addition salt form.

The steps (a) and (c) can be effected according to conventional methods, e.g. according to the following scheme which is illustrated in example 1 under (a) to (g). In this scheme $R_1$, $R_2$ and $R_3$ are as defined above and Hal is halogen, e.g. chlorine.

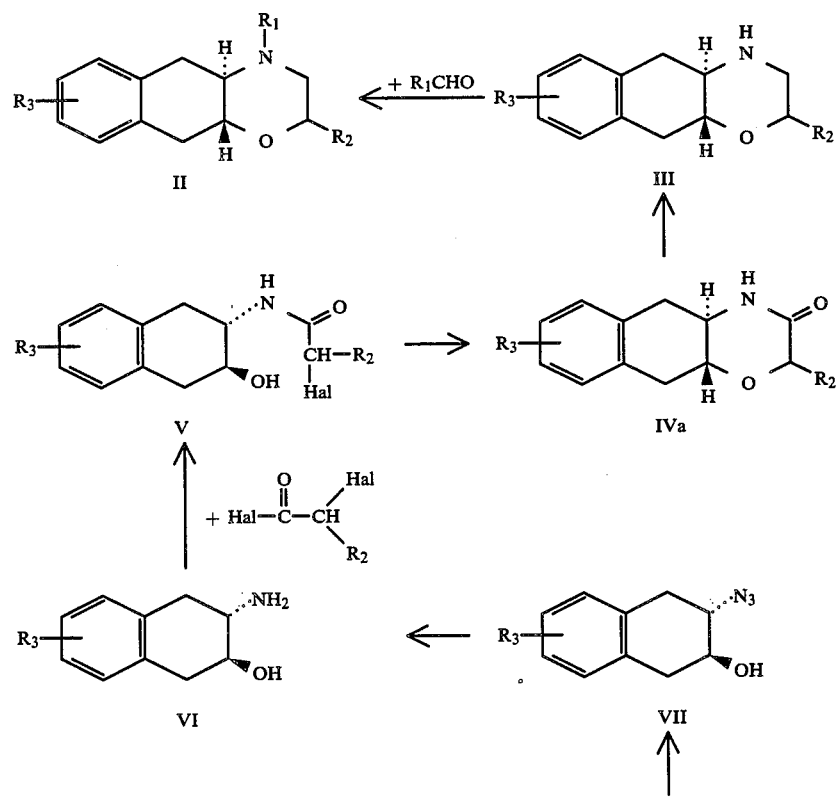

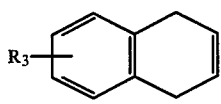

IX

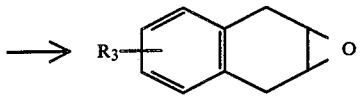

VIII

Step (d) can be effected as follows:
(a') for the production of a compound of formula Ia

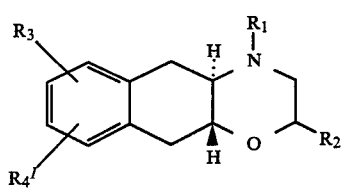

Ia wherein $R_1$, $R_2$ and $R_3$ are as defined above and $R_4{}^I$ is chlorine, bromine or iodine, introducing an halogen in a compound of formula II defined above, or (b') for the production of a compound of formula Ib

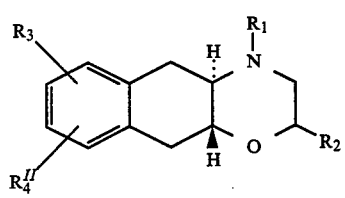

Ib wheren $R_1$, $R_2$ and $R_3$ are as defined above and $R_4{}^{II}$ is $(C_{1-4})$alkylthio or trifluoromethyl, replacing in a compound of formula Ia'

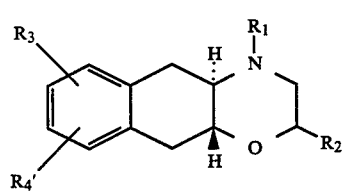

Ia' wherein $R_1$, $R_2$ and $R_3$ are as defined above and $R_4'$ is a leaving group, the leaving group $R_4'$ with a group $R_4{}^{II}$, or (c') for the production of a compound of formula Ic

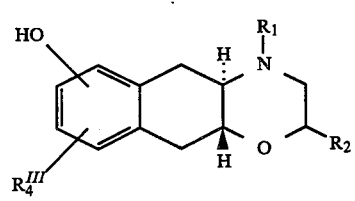

Ic wherein $R_1$ and $R_2$ are as defined above and $R_4{}^{III}$ is chlorine, bromine, iodine, $(C_{1-4})$alkylthio or trifluoromethyl, converting the alkoxy group of a compound of formula Id

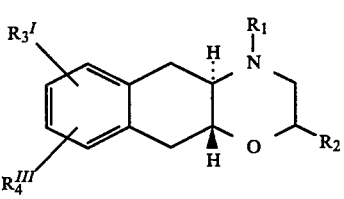

Id wherein $R_1$, $R_2$ and $R_4{}^{III}$ are as defined above and $R_3{}^I$ is $(C_{1-4})$alkoxy, into an hydroxy group, or (d') for the production of a compound of formula Ie

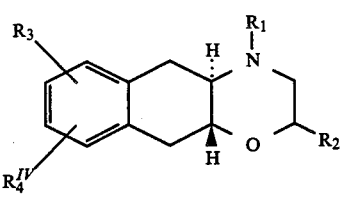

Ie wherein $R_1$, $R_2$ and $R_3$ are as defined above and $R_4{}^{IV}$ is $(C_{1-4})$alkylsulfoxide or $(C_{1-4})$alkylsulfone, oxidizing a compound of formula If

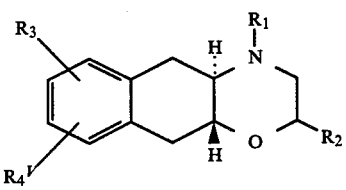

If wherein $R_1$, $R_2$ and $R_3$ are as defined above and $R_4{}^V$ is $(C_{1-4})$alkylthio, to the corresponding sulfoxide or sulfone,
and recovering the resultant compound of formula I in free base or acid addition salt form.

Introduction of halogen into compounds of formula II as in process (a') may take place in known manner, for example adding silver trifluoroacetate, in an aprotic solvent, e.g. methylene chloride.

Substitution of the leaving group $R_4'$ in the compounds of formula Ia' as in process (b') may take place in accordance with known methods. $R_4'$ being preferably halogen. Substitution of halogen by an alkylthio group occurs for example using the lithium salt of the corresponding thioalcohol with copper-I-oxide as the catalyst, in a dipolar-aprotic solvent, e.g. dimethylformamide, or also by means of a halogen-metal exchange using n-butyllithium, followed by reaction with the corresponding dialkyl disulphite or alkylthiosulphinic ester, in an aprotic solvent, e.g. tetrahydrofuran. Substitution of halogen by trifluoromethyl may take place for example using sodium trifluoroacetate.

The conversion of the alkoxy group into an hydroxy group as in process (c') may take place in accordance with usual methods, for example reacting the compound of formula Id with boron tribromide in an inert organic solvent, or by treatment with strong mineral acids, e.g. hydrobromic acid.

The oxidation is in process (d') may take place in accordance with known methods, e.g. using hydrogen peroxide.

Working up of the reaction mixtures obtained according to the above processes, and purification of the compounds of formula I thus obtained, may be effected in accordance with known methods.

The compounds of formula I may exist in free form or in the form of their addition salts with acids. Acid addition salts can be produced from the free base forms in known manner, and vice versa.

The starting compounds which are used for the processes described above consist in various 4a,10a-trans stereoisomers. Each of these processes may take place using starting compounds in form of the individual optically active isomers or their isomer mixtures, particularly their racemates, and leads to the corresponding end products.

The racemates may be separated into the individual optically active components, using known methods, e.g. formation of acid addition salts with optically active acids, e.g. (+)-[respect.(−)]-di-O,O'-p-toluolyl-D-(−)[respect.L-(+)]-tartaric acid, and fractionated cristallisation of the diastereoisomeric acid addition salts.

Insofar as the production of the starting products is not described, these are known, or they may be produced by known processes or in analogous manner to known processes. For example, the compound of formula IX, in which $R_3$ is methoxy, is described in German Published Specification No. 2 618 276.

The invention also comprises the starting compounds of formulae II, III, IV, V, VI, VII and VIII as defined above per se and the use of the compounds of formulae II, III and IV as pharmaceuticals.

The psychostimulating and/or antidepressant 3,4,4a,5,10,10a-hexahydro-2H-naphth[2,3-b]-1,4-oxazines and their pharmaceutically acceptable acid addition salts, hereinafter referred to as the compounds according to the invention, are novel and exhibit pharmacological activity and may therefore be used as pharmaceuticals.

They possess central, noradrenergic activity, which was demonstrated in the model of the rat with a bilaterally injured hypothalamus [Butterworth et al., Pharmacol. Bioch. Behaviour 8, 41 (1977)]. In this test, male animals having a weight of ca. 250 g are anaesthetised with Pentobarbital (40 mg/kg i.p.), and treated with 19.5 to 26 μg of 6-OH-dopamine in the anterior hypothalamus (duration of injection: 15 minutes). After three days, the behaviour in the observation cage and the motor response in the activitymeter are determined, and the material values compared statistically with control values.

In this test, doses of ca. 0.1 to 20 mg/kg p.o. of the compounds produce an antagonistic effect on the induced behaviour hypokinesia. Thus, e.g. with (−)-(4aR,10aR)-3,4,4a,5,10,10a-hexahydro-6-methoxy-4-methyl-9-methylthio-2H-naphth[2,3-b]-1,4-oxazine, the hypokinetic effect is reduced by 20% after 1 mg/kg p.o. and by 50% after 10 mg/kg p.o.

Furthermore in a concentration of 3-30 mg/kg p.o., the compounds inhibit the sedation of the rat which is induced by the sodium salt of diethyldithiocarbaminate (DDC, beta-hydroxylase inhibitor) [method according to Sulginiti et al., Psychopharmacology 51, 65 (1976)]. This inhibition is marked after administering the above-mentioned compound at 10 mg/kg p.o., and total at 30 mg/kg p.o. This activity similarly indicates central noradrenergic activity.

Moreover, in the sleep/wake cycle of the long-term implanted rat [Vigouret et al., Pharmacology 16 Suppl. A 156 (1978)], the compounds effect an increase in vigilance at 1 to 100 mg/kg p.o., by bringing about a lengthening of the wake phases. The increase in vigilance with the above-mentioned compound is e.g. 30% after 3 mg/kg p.o. and 70% after 10 mg/kg p.o.

The compounds according to the invention are therefore useful as psycho-stimulants for stimulating the central nervous system, in particular for increasing vigilance, and as anti-depressants for treating depressions.

For the above-mentioned application, the dosage to be used varies of course according to the substance used, the type of administration and the desired treatment. In general however, satisfactory results are obtained with doses of approximately 0.5 to 50 mg/kg body weight; administration may be effected with one daily dosage, or if necessary in several part doses.

For larger mammals, the daily dosage lies in the region of about 1 to 50 mg of the substance. Suitable forms of dosage generally contain from about 0.3 to about 50 mg of active substance, together with solid or liquid carrier substances or diluents.

The compounds according to the invention may be administered in similar manner to known standards for use in these utilities, for example co-dergocrine for the vigilance increasing indication. The suitable daily dosage for a particular compound will depend on a number of factors such as its relative potency of activity. It has for example been determined that the preferred compound of this invention which is the (−)-isomer of example 2 has a minimum effective dosis of 3 mg/kg p.o. in the above sleep/wake cycle test as compared to 10 mg/kg p.o. for co-dergocrine. It is therefore indicated that this compound may be administered at similar or lower dosages than conventionally employed for co-dergocrine.

Additionally for the antidepressant indication the compounds of the invention may be administered in similar manner to e.g. the known standard imipramine. Imipramine has a minimum effective dose of 5 mg/kg p.o. in the above sleep/wake cycle test and is employed at about 100 mg daily. It is therefore indicated that the (−)-isomer of example 2 may be administered at lower dosages than conventionally employed for imipramine, e.g. about 10 to 50 mg daily.

The present invention accordingly provides a compound according to the invention for use as a pharmaceutical, particularly for stimulating the central nervous system, in particular for increasing vigilance, and for treating depressions.

The compounds according to the invention may be administered in free base form or in pharmaceutically acceptable acid addition salt for. Such salts exhibit the same order of activity as the free bases. The present invention accordingly also provides a pharmaceutical composition comprising a compound according to the invention in association with a pharmaceutical carrier or diluent. Such compositions may be formulated in conventional manner so as to be for example a solution or a tablet.

The preferred compound is the (−)-(4aR,10aR)-3,4,4a,5,10,10a-hexahydro-6-methoxy-4-methyl-9-methylthio-2H-naphth[2,3-b]-1,4-oxazine.

In the following examples all temperatures are in degrees Centigrade and are uncorrected.

EXAMPLE 1 trans-3,4,4a,5,10,10a-hexahydro-9-iodo-6-methoxy-4-methyl-2H-naphth[2,3-b]-1,4-oxazine 3.27 g (0.014M) of trans-3,4,4a,10,10a-hexahydro-6-methoxy-4-methyl-2H-naphth[2,3-b]-1,4-oxazine and 3.09 g (0.014M) of silver trifluoroacetate are suspended in 100 ml of absolute methylene chloride. 3.43 g (0.027M) of iodine dissolved in 200 ml of absolute methylene chloride are subsequently added in drops over the course of 10 minutes. The reaction mixture is stirred for 3 hours at 20°, and is then filtered through a Hyflo filter. The residue of filtration is washed with 50 ml of methylene chloride. The methylene chloride solution is extracted with 50 ml of water, the organic phase dried and concentrated by evaporation. Trans-3,4,4a,5,10,10a-hexahydro-9-iodo-6-methoxy-4-methyl-2H-naphth[2,3-b]-1,4-oxazine is obtained as an oil. 1-H-NMR 90 MHz (CDCl3): δ=2.40 (S; 3H, N-CH3), 3.81 (s; 3H, O—CH3), 6.45 and 7.64 (AB, J=9 Hz; 2H, aromatic—H).

The starting material may be produced as follows:

(a)

1a,2,7,7a-tetrahydro-3-methoxy-naphth[2,3-b]oxirane 3.00 g (0.019M) of 1,4-dihydro-5-methoxynaphthalene are dissolved in 52 ml of methylene chloride, and cooled with an ice bath to 0°. 3.07 g (0.018M) of m-chloro-perbenzoic acid are subsequently added to this solution over the course of one minute. The ice bath is removed, and the reaction mixture is stirred for 15 hours at room temperature. The suspension is then added to a mixture of 20 ml of 10% sodium hydroxide and 40 g of ice. The organic phase is separated, and the aqueous phase is extracted twice, each time with 20 ml of methylene chloride. The combined organic phases are washed with water and sodium chloride solution, dried and concentrated by evaporation. 1a,2,7,7a-tetrahydro-3-methoxynaphth[2,3-b]oxirane is obtained (melting point 49.5°–50.5°, after purification by column chromatography, silica gel 0.063–0.200 mm, methylene chloride and recrystallisation from hexane).

(b)

trans-3-azido-1,2,3,4-tetrahydro-5-methoxy-2-naphthalinol 30.0 g (0.170M) of 1a,2,7,7a-tetrahydro-3-methoxynaphth[2,3-b]oxirane are dissolved in dimethyl sulphoxide. Furthermore, 90.0 g (1.384M) of sodium azide are suspended in DMSO and 19.5 g (0.200M) of concentrated sulphuric acid are dissolved in DMSO. The total quantity of DMSO is 1000 ml. The solutions and supensions are combined. Stirring subsequently takes place for 15 hours at 60°. 1500 ml of methylene chloride are then added to the reaction mixture. A suspension is obtained, which is filtered over Hyflo. The rose solution is concentrated by evaporation at 60° (10 torr), then at 80° (high vacuum 1/100 torr). Trans-3-azido-1,2,3,4-tetrahydro-5-methoxy-2-naphthalinol (m.p. 83°–84°) and its structural isomer trans-3-azido-1,2,3,4-tetrahydro-8-methoxy-2-naphthalinol (m.p. 145°–147°) are obtained in a ratio of 1:1. The structural isomers are separated by fractional crystallisation (methylene chloride/hexane).

(c)

trans-3-amino-1,2,3,4-tetrahydro-5-methoxy-2-naphthalinol 4.0 g of palladium on charcoal (10%) are coated with 100 ml of ethanol. 8.76 g (0.040M) of trans-3-azido-1,2,3,4-tetrahydro-5-methoxy-2-naphthalinol are dissolved in 100 ml of ethanol, and the solution is added to the catalyst suspension. The mixture is subsequently hydrogenated at 20° at 1.2 bar hydrogen pressure. Every 10 minutes for 50 minutes, the reaction vessel is emptied and rinsed with hydrogen. The reaction mixture is then filtered through a G 4 Hyflo suction filter. The catalyst is washed with methylene chloride and the filtrate concentrated by evaporation. Trans-3-amino-1,2,3,4-tetrahydro-5-methoxy-2-naphthalinol is obtained (m.p. 130°–132° after purification by column chromatography, silica gel, methylene chloride and 10% methanol).

(d)

trans-2-chloro-N-(1,2,3,4-tetrahydro-2-hydroxy-5-methoxy-3-naphthalinyl)acetamide 1.01 g (0.005M) of trans-3-amino-1,2,3,4-tetrahydro-5-methoxy-2-naphthalinol are dissolved in 50 ml of absolute methylene chloride. 0.81 g (0.008M) of triethylamine are added, and the mixture left to cool to 0°. At this temperature, 0.68 g (0.006M) of chloroacetyl chloride (dissolved in 5 ml of absolute methylene chloride) are then added in drops over the course of 5 minutes. Stirring is effected for 2 hours at room temperature. The reaction mixture is subsequently washed once with 1N hydrochloric acid and once with ice water. It is extracted three times, each with 20 ml of methylene chloride, the combined organic phases are dried, and the solvent is concentrated by evaporation. Trans-2-chloro-N-(1,2,3,4-tetrahydro-2-hydroxy-5-methoxy-3-naphthalinyl)-acetamide is obtained (m.p. 176°–178°, recrystallisation from methylene chloride/ether).

(e)

trans-2,4,4a,10,10a-hexahydro-6-methoxy-3H-naphth[2,3-b]-1,4-oxazine-3-one 0.86 g (0.036M) of sodium hydride and 0.24 g (0.652 mM) of tetrabutylammonium iodide are suspended in 100 ml of absolute tetrahydrofuran. A solution of 8.8 g (0.033M) of trans-2-chloro-N-(1,2,3,4-tetrahydro-2-hydroxy-5-methoxy-3-naphthalinyl)acetamide in 300 ml of absolute THF is subsequently added in drops at room temperature over the course of 15 minutes. Stirring is effected for 18 hours at room temperature, under an argon atmosphere. The solvent is subsequently concentrated by evaporation, and the residue taken up in methylene chloride/ice water (1:1, 100 ml). The aqueous phase is separated, and the organic phase is extracted with 20 ml each of 1N hydrochloric acid and water. The entire aqueous phases are again extracted with methylene chloride (twice, each time with 20 ml). The combined organic phases are dried and concentrated by evaporation. Trans-2,4,4a,5,10,10a-hexahydro-6-methoxy-3-naphth[2,3-b]-1,4-oxazin-3-one is obtained (m.p. 237°–240°, methylene chloride, acetone, ether).

(f)

trans-3,4,4a,5,10,10a-hexahydro-6-methoxy-2H-naphth[2,3-b]-1,4-oxazine 3.87 g (0.102M) of lithium aluminium hydride are suspended in 100 ml of absolute tetrahydrofuran. A solution of 5.93 g (0.025M) of trans-2,4,4a,5,10,10a-hexahydro-6-methoxy-3H-naphth[2,3-b]-1,4-oxazin-3-one in 300 ml of absolute THF is subsequently added in drops. The reaction mixture is refluxed for 2 hours and then cooled to −20°. 100 ml of ice water and 200 ml of methylene chloride are added, and stirring is effected for 15 minutes. The suspension is then filtered over Hyflo, the methylene chloride phase separated and the residue of filtration washed with 50 ml of methylene chloride. The combined organic phases are dried and concentrated by evaporation. Trans-3,3,4a,5,10,10a-hexahydro-6-methoxy-2H-naphth[2,3-b]-1,4-oxazine is obtained as an oil. 1-H-NMR 360 MHz (CDCl3): 67=2.34 (dd, J=12 and 17 Hz; 1H, c-5H axial), 3.81 (s; 3H, O—CH3).

(g)
trans-3,3,4a,5,10,10a-hexahydro-6-methoxy-4-methyl-2H-naphth[2,3-b]-1,4-oxazine 2 g of palladium on charcoal (10%) are suspended in 100 ml of methanol. To this are added 4.82 g (0.022M) of trans-3,4,4a,5,10,10a-hexahydro-6-methoxy-2H-naphth[2,3-b]-1,4-oxazine and 23.65 ml of formalin (37%), both dissolved in a total of 200 ml of methanol. The mixture is subsequently hydrogenated at 20°, at 1.2 bar hydrogen pressure. After 6 hours, the reaction mixture is filtered through a Hyflo suction filter, washed with 100 ml of methylene chloride, and the filtrate is concentrated by evaporation. The residue is taken up again in 100 ml of methylene chloride, and washed once each time with 20 ml of saturated potassium carbonate solution and water. The methylene chloride phase is dried and concentrated by evaporation. Trans-3,4,4a,5,10,10a-hexahydro-6-methoxy-4-methyl-2H-naphth[2,3-b]-1,4-oxazine is obtained (m.p. 268°–270°, recrystallisation from methylene chloride, methanol, acetone).

The following compounds of formula Ia are produced in analogous manner to example 1:

mixture is subsequently stirred for 5 hours at 80° under an argon atmosphere. The preparation is then filtered through Hyflo, washed with 20 ml of methylene chloride, and the filtrate is concentrated by evaporation. The residue is taken up in 30 ml of methylene chloride/30 ml of ice water, the organic phase is separated, and the aqueous phase is extracted three times, each with 10 ml of methylene chloride. The combined organic phases are dried and concentrated by evaporation. Trans-3,4,4a,5,10,10a-hexahydro-6-methoxy-4-methyl-9-methylthio-2H-naphth[2,3-b]-1,4-oxazine is obtained as an oil. The oil is purified by chromatography (silica gel, methylene chloride, 5% methanol). 1-H-NMR 90 MHz (CDCl3): δ=2.36 (s; 3H, N—CH3), 2.42 (s; 3H, S—CH3), 3.81 (s; 3H, O—CH3).

1.40 g (5.0 mM) of the compound thus obtained are dissolved in 50 ml of acetone and cooled to 0°. 2.75 ml (5.5 mM) of 2N ethereal hydrochloric acid are subsequently added whilst stirring. The precipitated salt is filtered off and washed with ether. Trans-3,4,4a,5,10,10a-hexahydro-6-methoxy-4-methyl-9-methylthio-2H-naphth[2,3-b]-1,4-oxazine hydrochloride is obtained (m.p. 238°–240° [decomposition], recrystallisation from acetone/ether).

Splitting of the racemic form:
4.96 g (17.8 mM) of trans-3,4,4a,5,10,10a-hexahydro-6-methoxy-4-methyl-9-methylthio-2H-naphth[2,3-b]-1,4-oxazine are dissolved in 150 ml of acetone. To this is added a solution of 7.19 g (17.8 mM) of (+)-di-O,O'-p-toluoyl-D-(−)-tartaric acid in 100 ml of acetone. The precipitating salt is stirred for one hour at room temperature and filtered off. The salt is recrystallised three times from methylene chloride/methanol (1:1). The salt is subsequently taken up in a mixture of 100 ml of ice water/10 ml of conc. ammonia/30 ml of methylene chloride. The organic phase is separated and the aqueous phase is extracted twice, each time with 20 ml of methylene chloride. The combined organic phases are dried and concentrated by evaporation. (−)-(4aR,-10aR)-3,4,4a,5,10,10a-hexahydro-6-methoxy-4-methyl-9-methylthio-2H-naphth[2,3-b]-1,4-oxazine is obtained as an oil and has a rotation value $[\alpha]_D^{20}$=−121.3° [c=0.52; methylene chloride/methanol (1:1)].

1.40 g (5.0 mM) of (−)-(4aR,10aR)-3,4,4a,5,10,10a-hexahydro-6-methoxy-4-methyl-9-methylthio-2H-naphth[2,3-b]-1,4-oxazine are dissolved in 50 ml of acetone and cooled to 0°. 2.75 ml (5.5 mM) of 2N ethereal hydrochloric acid are subsequently added whilst stirring. The precipitated salt is filtered off and washed with ether. (−)-(4aR,10aR)-3,4,4a,5,10,10a-hexahydro-6-methoxy-4-methyl-9-methylthio-2H-naphth[2,3-b]-1,4-oxazine hydrochloride is obtained (m.p. 237°–239°).

| Example | R1 | R2 | R3 (in 6) | R4I (in 9) | Racemate Antipode | m.p. (Hydrochloride) |
|---|---|---|---|---|---|---|
| 1b | —CH2CH3 | H | —OCH3 | Br | racemate | 300° |
| 1c | —(CH2)2—CH3 | " | " | " | " | 256–258° |
| 1d | —CH3 | —CH3 | " | " | " | 283–284° |
| 1e | " | H | " | Cl | " | 286–287° |
| 1f | " | H | " | Br | " | 286–287° |
| 1g | " | —CH2CH3 | " | " | " | 285–286° |
| 1h | " | " | " | Cl | " | 230° (decomp.) |
| 1i | " | " | " | I | " | 268–270° |
| 1j | —CH2CH3 | —CH3 | " | " | " | 271–272° |
| 1k | —CH3 | H | Br | —OCH3 | " | 263–265° (decomp.) |
| 1l | " | " | I | —OCH3 | " | 284–286° (decomp.) |
| 1m | " | " | —OCH3 | I | (+) | 284–286° |
| 1n | " | " | " | " | (−) | 284–286° |

EXAMPLE 2
trans-3,4,4a,5,10,10a-hexahydro-6-methoxy-4-methyl-9-methylthio-2H-naphth[2,3-b]-1,4-oxazine (racemate) and
(−)-(4aR,10aR)-3,4,4a,5,10,10a-hexahydro-6-methoxy-4-methyl-9-methylthio-2H-naphth[2,3-b]-1,4-oxazine 0.44 g (1.2 mM) of trans-3,4,4a,5,10,10a-hexahydro-9-iodo-6-methoxy-4-methyl-2H-naphth[2,3-b]-1,4-oxazine (for production see example 1), dissolved in 5 ml of DMF, as well as 2.34 g (16.3 mM) of copper-I-oxide, are added to a suspension of 0.53 g (9.8 mM) of methylthiolithium in 10 ml of dimethylformamide. The reaction Recrystallisation from acetone/ether, with the rotation value $[\alpha]_D^{20} = -117.4°$ [c=0.52; methylene chloride/methanol (1:1)].

The following compounds of formula Ib are produced in analogous manner to example 2:

| Example | $R_1$ | $R_2$ | $R_3$ (in 6) | $R_4$II (in 9) | Racemate Antipode | m.p. |
|---|---|---|---|---|---|---|
| 2b | H | H | —OCH$_3$ | —SCH$_3$ | racemate | 192–194[1] |
| 2c | —CH$_3$ | " | " | " | (+) | 245–247°[2] |
| 2d | " | —CH$_3$ | " | " | racemate | 211–213°[2] |
| 2e | —(CH$_2$)$_2$CH$_3$ | H | " | " | " | 242–244°[2] |
| 2f | —CH$_2$CH$_3$ | " | " | " | " | 238–239°[2] |
| 2g | —CH$_3$ | " | " | —SCH$_2$CH$_3$ | " | 209–210°[2] |
| 2h | " | —CH$_2$CH$_3$ | " | —SCH$_3$ | " | 210–212°[2] |
| 2i | " | —(CH$_2$)$_2$CH$_3$ | " | " | " | 269–270°[2] |
| 2j | —CH$_2$CH$_3$ | —CH$_3$ | " | " | " | 231–232°[2] |
| 2k | —CH$_3$ | H | —SCH$_3$ | —OCH$_3$ | " | 255–256°[2] |
| 2l | " | " | —OCH$_3$ | —SCH(CH$_3$)$_2$ | " | 214°[2] |

[1]Hydrogen maleate
[2]Hydrochloride

EXAMPLE 3 trans-3,4,4a,5,10,10a-hexahydro-6-hydroxy-4-methyl-9-methylthio-2H-naphth[2,3-b]-1,4-oxazine 1.63 g (5.84 mM) of trans-3,4,4a,5,10,10a-hexahydro-6-methoxy-4-methyl-9-methylthio-2H-naphth[2,3-b]-1,4-oxazine (for production see example 2) are dissolved in 65 ml of methylene chloride and the solution is cooled to −40° under an argon atmosphere. 29 ml (29 mM) of a 1M boron tribromide solution in methylene chloride are then added over the course of 10 minutes. The reaction mixture is left to reach room temperature and stirred 15 hours. The reaction product is then poored on ice and extracted once with 15 ml of 10% sodium carbonate solution and once with 15 ml of water. The organic phase is dried and concentrated by evaporation. The crude product is taken up in 30 ml of acetone and 10 ml of ethereal hydrochloric acid (2N) are added. The precipitated salt is filtered off. The hydrochloride of the title compound is obtained. M.p. 250° (decomposition), recrystallisation from methanol/acetone.

Trans-3,4,4a,5,10,10a-hexahydro-6-hydroxy-4-methyl-2H-naphth[2,3-b]-1,4-oxazine is produced in analogous manner to example 3. M.p. of the hydrochloride: 310°–312° (decomposition).

EXAMPLE 4 trans-3,4,4a,5,10,10a-hexahydro-6-methoxy-4-methyl-9-methylsulfoxide-2H-naphth[2,3-b]-1,4-oxazine 2.79 g (10 mM) of trans-3,4,4a,5,10,10a-hexahydro-6-methoxy-4-methyl-9-methylthio-2H-naphth[2,3-b]-1,4-oxazine (for production see example 2) are dissolved in 10 ml methylene chloride and 1.90 g (10 mM) p-toluenesulfonic acid hydrate are added. After cooling to 0° a solution of 1.7 g (10 mM) m-chloroperbenzoic acid in 20 ml of methylene chloride is added dropwise in such a manner that the reaction temperature does not exceed 5°. After complete addition stirring is effected for 1 hour at 0° and for 2 hours at room temperature. 10 ml of a saturated sodium hydrogenocarbonate solution are subsequently added and the organic phase is extracted with methylene chloride/water. The combined methylene chloride phases are dried and concentrated by evaporation. The residue is chromatographed (silica gel/methylene chloride/5% methanol). The eluate of the sulfoxide is concentrated by evaporation, taken up in 40 ml of acetone and 5 ml of ethereal hydrochloric acid (2N) are added. The precipitated salt is filtered off and the hydrochloride of the title compound is obtained. M.p. 200° (decomposition), recrystallisation from methylene chloride/acetone/ether.

What we claim is:

1. A compound which is of formula I

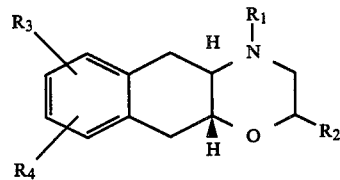

wherein
$R_1$ and $R_2$ independently are hydrogen or (C$_{1-4}$)alkyl,
$R_3$ is hydroxy or (C$_{1-4}$)alkoxy and
$R_4$ is (C$_{1-4}$)alkylthio, (C$_{1-4}$)alkylsulfoxide, (C$_{1-4}$)alkylsulfone, chlorine, bromine, iodine or trifluromethyl,
in free base or acid addition salt form.

2. A compound of claim 1 wherein
$R_1$ and $R_2$ independently are hydrogen or (C$_{1-4}$)alkyl,
$R_3$ and $R_4$ are in para position,
$R_3$ is (C$_{1-4}$)alkoxy and
$R_4$ is chlorine, bromine, iodine or (C$_{1-4}$)alkylthio,
in free base or acid addition salt form.

3. A compound of claim 1 wherein
$R_1$ is (C$_{1-4}$)alkyl,
$R_2$ is hydrogen,
$R_3$ is (C$_{1-4}$)alkoxy and
$R_4$ is chlorine, bromine, iodine or (C$_{1-4}$)alkylthio,
in free base or acid addition salt form.

4. A compound of claim 1 wherein $R_1$ is methyl, $R_2$ is hydrogen, $R_3$ is methoxy and $R_4$ is methylthio, in form of the (−)-isomer, in free base or acid addition salt form.

5. The compound of claim 1 which is trans-3,4,4a,5,10,10a-hexahydro-9-iodo-6-methoxy-4-methyl-2H-naphth[2,3-b]-1,4-oxazine in free base form or acid addition salt form.

6. The compound of claim 1 in racemate form in which $R_1$, $R_2$, $R_3$ and $R_4$ are
(a) —CH$_2$CH$_3$, H, 6—OCH$_3$ and 9—Br
(b) —(CH$_2$)$_2$—CH$_3$, H, 6—OCH$_3$ and 9—Br;
(c) —CH$_3$, —CH$_3$, 6—OCH$_3$ and 9—Br;
(d) —CH$_3$, H, 6—OCH$_3$ and 9—Cl;
(e) —CH$_3$, H, 6—OCH$_3$ and 9—Br;
(f) —CH$_3$, —CH$_2$CH$_3$, 6—OCH$_3$ and 9—Br;
(g) —CH$_3$, —CH$_2$CH$_3$, 6—OCH$_3$ and 9—Cl;

(h) —CH$_3$, —CH$_2$CH$_3$, 6—OCH$_3$ and 9—I;
(i) —CH$_2$CH$_3$, —CH$_3$, 6—OCH$_3$ and 9—I;
(j) —CH$_3$, H, 6—Br and 9—OCH$_3$;
(k) —CH$_3$, H, 6—I and 9—OCH$_3$
in free base form or acid addition salt form.

7. The compound of claim 1 in (+) antipode form in which R$_1$, R$_2$, R$_3$ and R$_4$ are —CH$_3$, H, 6—OCH$_3$ and 9—I in free base form or acid addition salt form.

8. The compound of claim 1 in (−) antipode form in which R$_1$, R$_2$, R$_3$ and R$_4$ are —CH$_3$, H, 6—OCH$_3$ and 9—I in free base form or acid addition salt form.

9. The compound of claim 1 in racemate form which is trans-3,4,4a,5,10,10a-hexahydro-6-methoxy-4-methyl-9-methylthio-2H-naphth[2,3-b]-1,4-oxazine in free base form or acid addition salt form.

10. The compound of claim 1 which is (−)-(4aR,-10aR)-3,4,4a,5,10,10a-hexahydro-6-methoxy-4-methyl-9-methylthio-2H-naphth[2,3-b]-1,4-oxazine in free base form or acid addition salt form.

11. The compound of claim 1 in racemate form in which R$_1$, R$_2$, R$_3$ and R$_4$ are
(a) H, H, 6—OCH$_3$ and 9—SCH$_3$;
(b) —CH$_3$, —CH$_3$, —6OCH$_3$ and 9—SCH$_3$;
(c) —(CH$_2$)$_2$CH$_3$, H, 6—OCH$_3$ and 9—SCH$_3$;
(d) —CH$_2$CH$_3$, H, 6—OCH$_3$ and 9—SCH$_3$
(e) —CH$_3$, H, 6—OCH$_3$ and 9—SCH$_2$CH$_3$;
(f) —CH$_3$, CH$_2$CH$_3$, 6—OCH$_3$, 9—SCH$_3$
(g) —CH$_3$, —(CH$_2$)$_2$CH$_3$, 6—OCH$_3$, 9—SCH$_3$;
(h) —CH$_2$CH$_3$, —CH$_3$, 6—OCH$_3$, 9—SCH$_3$;
(i) —CH$_3$, H, 6—SCH$_3$, 9—OCH$_3$; and
(j) —CH$_3$, H, 6—OCH$_3$, 9—SCH(CH$_3$)$_2$
in free base form or acid addition salt form.

12. The compound of claim 1 in (+) antipode form in which R$_1$, R$_2$, R$_3$ and R$_4$ are —CH$_3$, H, 6—OCH$_3$ and 9—SCH$_3$ in free base form or acid addition salt form.

13. The compounds of claim 1 which is trans-3,4,4a,5,10,10a-hexahydro-6-hydroxy-4-methyl-9-methylthio-2H-naphth[2,3-b]-1,4-oxazine in free base form or acid addition salt form.

14. The compound of claim 1 which is trans-3,4,4a,5,10,10a-hexahydro-6-methoxy-4-methyl-9-methylsulfoxide-2H-naphth[2,3-b]-1,4-oxazine in free base form or acid addition salt form.

15. A pharmaceutical composition comprising a compound according to claim 1 in pharmaceutically acceptable form, in association with a pharmaceutical carrier or diluent.

16. A method of stimulating the central nervous system or increasing vigilance in a subject in need of such treatment, which comprises administering a therapeutically effective amount of a compound of claim 1 in pharmaceutically acceptable form.

17. A method of treating a subject suffering from depressions, which comprises administering a therapeutically effective amount of a compound of claim 1 in pharmaceutically acceptable form.

* * * * *